United States Patent [19]

Bell et al.

[11] 4,028,464

[45] June 7, 1977

[54] FUNGICIDE COMPOSITIONS FOR THE CONTROL OF SNOWMOLD

[75] Inventors: Robert Joseph Bell; James Almy Simmons, both of Marysville, Ohio

[73] Assignee: The O. M. Scott & Sons Company, Marysville, Ohio

[22] Filed: Nov. 24, 1975

[21] Appl. No.: 634,907

Related U.S. Application Data

[63] Continuation of Ser. No. 397,826, Sept. 17, 1973, abandoned.

[52] U.S. Cl. .............................. 424/273; 424/300; 424/341
[51] Int. Cl.$^2$ .................. A01N 9/12; A01N 9/22; A01N 9/24
[58] Field of Search ............ 424/273, 300, 341

[56] References Cited

UNITED STATES PATENTS

| | | | |
|---|---|---|---|
| 2,933,504 | 4/1960 | Klopping | 424/273 X |
| 3,265,564 | 8/1966 | Scribner et al. | 424/341 X |
| 3,631,176 | 12/1971 | Klopping | 424/273 X |

OTHER PUBLICATIONS

Pesticide Manual, British Crop Protection Council, 3rd Ed., 1972, p. 474, (1972).

*Primary Examiner*—Leonard Schenkman
*Attorney, Agent, or Firm*—J. B. Raden; H. J. Holt

[57] ABSTRACT

A fungicide composition for the control of plant disease comprising (a) a substituted methoxybenzene and (b) a benzimidazolecarbamate or a compound which breaks down upon application to plants to form a benzimidazolecarbamate, the ratio by weight of the methoxybenzene to the benzimidazolecarbamate ranging from 10:1 to 1:5. The compositions are particularly effective for the control of both gray and pink snowmold.

11 Claims, No Drawings

FUNGICIDE COMPOSITIONS FOR THE CONTROL OF SNOWMOLD

This is a continuation of application Ser. No. 397,826, filed Sept. 17, 1973, now abandoned.

This invention relates to a fungicide composition and to a process for the control of plant disease therewith.

Typhula blight and Fusarium Patch, known as gray and pink snowmold respectively, are severe disease problems with turfgrasses. It is known that gray snowmold, *Typhula spp.*, may be controlled by the application of the compound 1,4-dichloro-2,5-dimethoxybenzene. At relatively high application rates, this compound also controls pink snowmold, *Fusarium nivale*. It is also known that pink snowmold can be controlled with certain benzimidazolecarbamates, such as methyl 1-(butylcarbamoyl)-2-benzimidazolecarbamate. The fungicidal activity of substituted methoxybenzene compounds is disclosed in U.S. Pat. No. 3,265,564. The fungicidal activity of carbamoyl substituted 2-aminobenzimidazoles is disclosed in U.S. Pat. No. 3,631,176. The latter patent also suggests that the benzimidazoles are compatible with a large number of other fungicides.

Pink and gray snowmold frequently occur together and it is of course desirable to control both fungi with the application of a single composition. However, the blending of two or more compounds, even though compatible, in a single fungicide composition normally results at best in simply providing for the additive effect of the individual compounds and in many instances results in inhibiting the effectiveness of the individual compounds.

It is an object of the present invention to provide a single composition which is more effective in combination for the control of both gray and pink snowmold than the additive effect of individual compounds of which it is composed.

It is a more specific object of this invention to provide a fungicide composition for the control of a broad spectrum of turfgrass fungi including, but not limited to, gray and pink snowmold.

It has now been found that a blend of certain proportions of (a) a substituted methoxybenzene and (b) a benzimidazolecarbamate, or a compound which, upon application to plants, breaks down to form a benzimidazolecarbamate, controls both pink and gray snowmold more effectively in combination than either compound used individually. In most instances, the compositions of the invention achieve in combination more complete control of snowmold than twice the amount of the individual compounds. These results are believed totally unpredictable from a knowledge of either the compatibility of the compounds or of the properties or results previously achieved with either of these compounds alone. Moreover, the blend of fungicides are highly effective not only for pink and gray snowmold control, but also for the control of other fungi, including dollarspot, pythium, stripe smut and *Fusarium roseum*. The aforementioned U.S. Pat. No. 3,631,176 lists 1,4-dichloro-2,5-dimethoxybenzene as illustrative of one of a vast number of chemicals which may used with benzimidazole fungicides. However, there is no recognition in the patent that a blend of the two compounds, particularly a blend of certain proportions of the two compounds, will effectively control both pink and gray snowmold, nor that such a blend will have greater effectiveness than either compound alone for each snowmold. In short, the two compounds together achieve a truly synergistic control of pink and gray snowmold.

More specifically, the invention is directed to a fungicide composition comprising a. a compound of the formula

FORMULA I

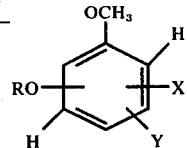

wherein R is selected from the group consisting of methyl and ethyl;

X is selected from the group consisting of fluorine, chlorine, bromine, methyl, ethyl, and methoxy; and Y is selected from the group consisting of fluorine, chlorine, bromine and methyl, and (b) a benzimidizolecarbamate or a compound which, when applied to plants, breaks down to form a benzimidizolecarbamate, the ratio of weight of compound (a) to compound (b) ranging from 10:1 to 1:5. A preferred ratio of compound (a) to compound (b) is 4:1 to 1:1. The invention is also directed to a process for the control of plant disease, and particularly turfgrass disease, by the application to the turf of a fungicidally effective amount of the foregoing composition.

In Formula I above, a preferred class of methoxybenzene compounds is that in which R is methyl and X and Y are both chlorine. A particularly suitable compound is 1,4-dichloro-2,5-dimethoxybenzene, commercially available under the name Chloroneb. The preparation of this and other useful methoxybenzene compounds is disclosed in the aforementioned U.S. Pat. No. 3,265,564.

Benzimidazolecarbamate compounds useful in the invention may be represented by the formula Formula II
(a)

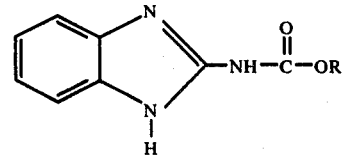

wherein R is methyl, ethyl, isopropyl or sec-butyl. These compounds also exist in an isomeric form represented by the formula Formula II
(b)

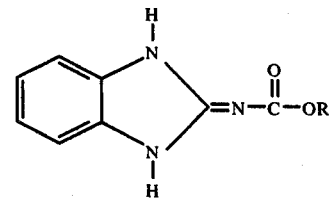

wherein R is the same as in Formula II (a). However the dominant form is isomer (a). A suitable example of a compound of Formula II is methyl 2-benzimidazolecarbamate. The compounds of Formula II are believed to be the active fungicidal ingredient forming the second component (compound (b)) of the invention.

In addition to compounds of Formula II, it is known that a variety of compounds will, upon application to plants, break down to form the benzimidazoles of Formula II. One such group of compounds is that in which either or both cyclic nitrogens in Formula II is bonded to a carbamoyl group, a carbonyl containing group, a thionyl or a thiocarbonyl group. This group of compounds, all of which breakdown to form benzimidazoles of the type illustrated by Formula II, may be represented by the formula.

Formula III
(a)

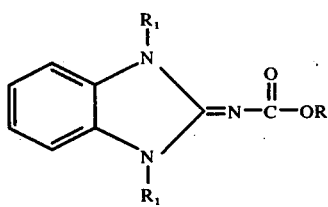

wherein R is the same as in Formula II and $R_1$ is one of the aforementioned groups substituted on one or both of the cyclic nitrogens. These compounds also exist in an isomeric form represented by the formula.

Formula III
(b)

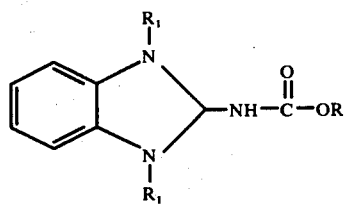

wherein R and $R_1$ are the same as in Formula III (a). The dominant form is that of isomer (a). In Formula III, the two $R_1$ groups may be the same or different and may be hydrogen, carbamoyl, acetyl, carboalkoxy, carboaryloxy, benzoyl, thiocarbonyl or thionyl. More specifically, $R_1$ may be

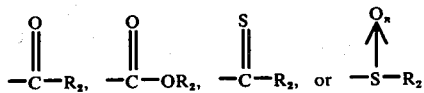

in which $R_2$ is alkyl, cycloalkyl, aryl or aralkyl and $n$ is 0, 1 or 2 or a carbamoyl group of the formula

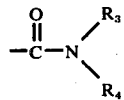

wherein $R_3$ is hydrogen, alkyl of 1 through 6 carbon atoms, alkenyl of 3 through 6 carbon atoms or alkynyl of 3 through 6 carbon atoms; and $R_4$ is alkyl of 1 through 12 carbon atoms; phenyl; phenyl substituted with methyl, ethyl, methoxy, ethoxy, nitro, cyano or halogen; benzyl; benzyl substituted with methyl, nitro, methoxy or halogen; (cycloalkyl) alkyl of 7 through 8 carbon atoms; (cycloalkyl) alkyl of 7 through 8 carbon atoms substituted with methyl; cyclohexyl; cyclohexyl substituted with methyl; alkenyl of 3 through 10 carbon atoms; (alkoxycarbonyl) alkyl of 3 through 6 carbon atoms; or alkenyl of 3 through 6 carbon atoms. A suitable example of a carbamoyl substituted compound is methyl 1-(butylcarbamoyl)-2-benzimidazolecarbamate. Other examples of substituted carbamoyl compounds of Formula III as well as their preparation are disclosed in the aforementioned U.S. Pat. No. 3,631,176.

In addition to the compounds of Formula III, thiophanates also hydroloyze and cyclize to benzimidazolecarbamates when they are applied to plants and are accordingly useful in the invention. Such compounds may be represented by the formula Formula IV

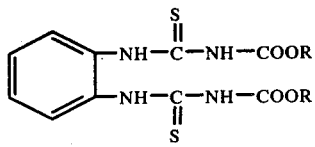

in which R is a lower alkyl group of from one to four carbon atoms. A particularly useful thiophanate is thiophanate methyl [1,2-di-(3-methyoxycarbonyl-2-thioureido) benzene].

Compounds of the type shown in Formulas III and IV will, as indicated above, break down to benzimidazolecarbamates in the presence of moisture when applied to plants or turf. The degradation reaction will occur at all ambient temperatures (e.g. from 0° to 100° F). It is possible that compounds, other than those specifically illustrated, may also form benzimidazolecarbamates upon application to plants and all such compounds are within the scope of the invention. It is only necessary that compounds of Formula II be used as such or be formed in situ.

In its preferred form, the fungicide compositions of the invention comprise a granular mixture of the following ingredients in the following proportions based on an amount used to treat 10,000 sq. ft. of turf or plant area:

a. from 142 to 284 grams (about 0.5 to 1 oz./1000 sq. ft.) of a benzimidazole, preferably either methyl 1-(butylcarbamoyl)-2-benzimidazolecarbamate or methyl 2-benzimidazolecarbamate.
b. from 283 to 436 grams (about 1 to 2 oz./1000 sq. ft.) of a substituted methoxybenzene, preferably 1,4-dichloro-2,5-dimithoxybenzene.
c. from 50 to 2000 milliliters of a sticking agent, such as a lower aliphatic glycol or a polybutene polymer, and
d. a particulate carrier.

Proportions for treating other than 10,000 sq. ft. of turf area would require proportionately more or less of the named ingredients. The carrier may be an inert particulate material such as vermiculite, altapulgite, rice hulls, corncobs or other known carrier material or an active ingredient such as fertilizer. It should be used in an amount sufficient to give a flowable composition. Normally the weight of carrier will be in excess of the weight of fungicide, preferably an amount varying from 4 to 16 times the combined weight of fungicides.

The compositions are prepared by mixing together the fungicide compounds and feeding the mixed compounds into a blender containing the inert carrier or fertilizer while the blender is agitating. Simultaneously, the sticking agent solution is sprayed onto the solids mixture.

The fungicide compositions of the invention are preferably applied to turf by, for example, use of a lawn spreader at a setting which will apply from .5 to 1 oz. of the benzimidazole and from 1 to 2 oz. of the methoxybenzene to 1000 sq. ft. of turf. The fungicides may also be applied in other convenient forms which are well known, as for example, wettable powders and flowable liquid concentrates.

Diluents, stabilizers, surfactants, plant nutrients, flow enhancing agents, adhesives, dyes and other adjuvants may also be employed to produce formulations with the compositions of the invention. These and other adjuvants which may be employed are described in *Chemistry of the Pesticides* (3rd Edition), Frear, D. Van Nostrand Company, Inc., New York, N.Y. 1955, incorporated herein by reference.

The following examples illustrate the practice of the invention:

EXAMPLE 1

A preblend of 436.3 grams of Chloroneb and 283.5 grams of Benomyl fungicide powders was prepared. Chloroneb is a commercially available mixture of 65% 1,4-dichloro-2,5-dimethoxybenzene and 35% inert atapulgite or other particulate clay carrier. Renomyl is a commerically available mixture of 50% methyl 1-(butylcarbamoyl)-2-benzimidazolecarbamate and 50% sucrose carrier. This preblend was fed dry into a blender containing 15 lbs. of particulate corncob while the blender was agitated. Simultaneously 600 ml of Polyvis OSH solution was sprayed onto the solids mixture and the mixture thoroughly blended. (Polyvis OSH is a trademark for polybutene polymer having a specific gravity of 0.837, a viscosity index of 65, a viscosity at 100° F of 150 and at 210° F of 42).

EXAMPLES 2–6

A series of additional fungicide compositions were prepared in accordance with the procedure of Example 1 but containing only a single fungicide, or containing a combination of fungicides outside the scope of the invention. The compositions were as follows:

| Example | Fungicide | Carrier | Sticking Agent |
|---|---|---|---|
| 2. | Chloroneb | Vermiculite | Polyvis OSH |
| 3. | Benomyl | Corncob | Polyvis OSH |
| 4. | Thiram | Corncob | Polyvis OSH |
| 5. | Benomyl & Thiram | Corncob | Polyvis OSH |

Thiram is tetramethyl thiuramdisulfide, a commercially available fungicide recommended for snowmold control.

A series of tests were conducted with the foregoing compositions to compare their effectiveness for the control of gray and pink snowmold. The tests were carried out on 4 ft. × 10 ft. plots of Penncross bentgrass infested with both gray and pink snowmold. Control plots, (2 ft. × 10 ft.) of the same grass were left untreated. Table I records the results of these test on both the untreated and treated plots.

TABLE I

| | Fungicide | Rate Oz./1,000 sq. ft. | Average % Disease Coverage | | | Average % Control | |
|---|---|---|---|---|---|---|---|
| | | | Gray | Pink | Color* | Gray | Pink |
| 1. | Chloroneb Benomyl | 2 1 | 0 | 0 | 10 | 100 | 100 |
| 2. | Untreated | | 57 | 28 | 6 | 0 | 0 |
| 3. | Chloroneb | 6 | 0 | T** | 9 | 100 | 99 |
| 4. | Untreated | | 43 | 32 | 7 | 0 | 0 |
| 5. | Benomyl | 1 | 45 | 3 | 6 | 25 | 99 |
| 6. | Untreated | | 60 | 25 | 6 | 0 | 0 |
| 7. | Thiram | 8 | 26 | 29 | 7 | 57 | 9 |
| 8. | Untreated | | 60 | 32 | 6 | 0 | 0 |
| 9. | Benomyl Thiram | 1 2 | 53 | 14 | 6 | 7 | 32 |
| 10. | Untreated | | 57 | 23 | 6 | 0 | 0 |
| 11. | Benomyl Thiram | 2 4 | 53 | 23 | 6 | 7 | 18 |
| 12. | Untreated | | 57 | 28 | 6 | 0 | 0 |

*1–10 scale, best color is 10.
**T=Trace.

The results of Table I indicate that the combination fungicide compositions of the invention achieved 100% control of both gray and pink snowmold, a result better than that achieved with over twice the combined amounts of Chloroneb and Benomyl used separately (Examples 3 and 5). The combination of Benomyl with a known fungicide (Examples 9 and 11) was considerably less effective, even at double the rate, than the combination fungicide of the invention. In both snowmold control and turf color, the best results were achieved with the combination fungicide composition of the invention.

We claim:
1. A fungicidal composition for the control of snowmold comprising
   a. 1,4-dichloro-2,5-dimethoxybenzene and
   b. a compound selected from the group consisting of
      1. a benzimidazole of the formula

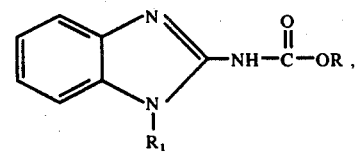

a benzimidazole of the formula

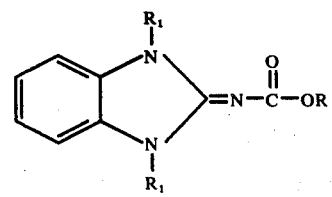

wherein R is selected from the group consisting of methyl and ethyl; and R₁ is selected from the group consisting of hydrogen and butyl carbamoyl, and 2. a thiophanate of the formula

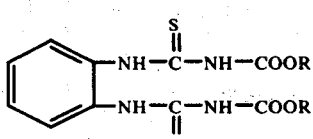

in which R is selected from the group consisting of methyl and ethyl, the ratio by weight of compound (a) to compound (b) ranging from 10:1 to 1:1.

2. The composition of claim 1 in which compound (b) is methyl 2-benzimidazolecarbamate.

3. The composition of claim 1 in which compound (b) is methyl 1-(butylcarbamoyl)-2-benzimidazolecarbamate.

4. The composition of claim 1 in which compound (b) is thiophanate methyl.

5. The fungicidal composition of claim 1 in which the ratio by weight of compound (a) to compound (b) is from 4:1 to 1:1.

6. A fungicidal composition for the control of snowmold comprising
a. 1,4-dichloro-2,5-dimethoxybenzene and
b. a compound selected from the group consisting of
 1. methyl 2-benzimidazolecarbamate,
 2. methyl 1-(butylcarbamoyl)-2-benzimidazolecarbamate, and
 3. thiophanate methyl,
the ratio by weight of compound (a) to compound (b) being 2 to 1.

7. The composition of claim 6 in which compound (b) is methyl 2-benzimidazolecarbamate.

8. The composition of claim 6 in which compound (b) is methyl 1-(butylcarbamoyl)-2-benzimidazolecarbamate.

9. The composition of claim 6 in which compound (b) is thiophanate methyl.

10. A process for the control of snowmold in plants comprising applying to said plants a fungicidally effective amount of a composition comprising
a. 1,4-dichloro-2,5-dimethoxybenzene and
b. a compound selected from the group consisting of 1. a benzimidazole of the formula

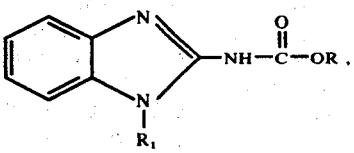

a benzimidazole of the formula

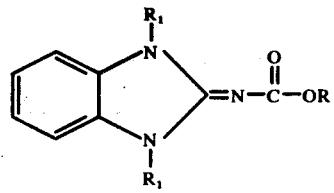

wherein R is selected from the group consisting of methyl and ethyl; and $R_1$ is selected from the group consisting of hydrogen and butyl carbamoyl, and (2) a thiophanate of the formula

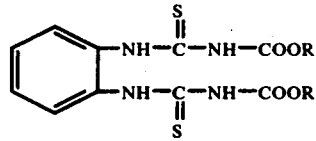

in which R is selected from the group consisting of methyl and ethyl, the ratio by weight of compound (a) to compound (b) ranging from 10:1 to 1:1.

11. The process of claim 10 in which compound (b) is

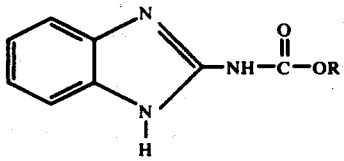

wherein R is selected from the group consisting of methyl and ethyl.

* * * * *